United States Patent
Simon

(10) Patent No.: US 7,361,165 B2
(45) Date of Patent: Apr. 22, 2008

(54) PRESSURE COMPENSATING IV FLOW CONTROL REGULATOR

(76) Inventor: Michael G. Simon, 7854 Sitio Coco, Carlsbad, CA (US) 92009

( * ) Notice: Subject to any disclaimer, the term of this patent is extended or adjusted under 35 U.S.C. 154(b) by 383 days.

(21) Appl. No.: 10/342,797

(22) Filed: Jan. 15, 2003

(65) Prior Publication Data
US 2003/0135164 A1    Jul. 17, 2003

Related U.S. Application Data

(60) Provisional application No. 60/349,834, filed on Jan. 16, 2002.

(51) Int. Cl.
*A61M 5/00* (2006.01)
(52) U.S. Cl. .................................... 604/246
(58) Field of Classification Search ............. 604/246, 604/247, 248, 251, 256, 288.03; 138/43
See application file for complete search history.

(56) References Cited

U.S. PATENT DOCUMENTS

| | | | | |
|---|---|---|---|---|
| 3,207,641 A | * | 9/1965 | Simko, Jr. et al. | 156/175 |
| 3,806,086 A | * | 4/1974 | Cloyd | 251/149.7 |
| 3,841,354 A | * | 10/1974 | McDonnell | 138/43 |
| 3,957,082 A | * | 5/1976 | Fuson et al. | 137/625.41 |
| 4,146,055 A | * | 3/1979 | Ryder et al. | 137/625.41 |
| 4,504,263 A | | 3/1985 | Steuer et al. | |
| 4,515,588 A | * | 5/1985 | Amendolia | 604/118 |
| 4,589,872 A | * | 5/1986 | Bellin et al. | 604/246 |
| 4,634,434 A | * | 1/1987 | Marino et al. | 604/246 |
| 4,769,012 A | * | 9/1988 | Quang et al. | 604/247 |
| 4,822,344 A | * | 4/1989 | O'Boyle | 604/248 |
| 4,925,451 A | | 5/1990 | Amendolia | |
| 5,113,904 A | * | 5/1992 | Aslanian | 137/556 |
| 5,190,527 A | | 3/1993 | Hamilton et al. | |
| 5,234,413 A | * | 8/1993 | Wonder et al. | 604/248 |
| 5,240,035 A | | 8/1993 | Aslanian et al. | |
| 5,241,985 A | | 9/1993 | Faust et al. | |
| 5,520,661 A | | 5/1996 | Lal et al. | |
| 5,730,730 A | | 3/1998 | Darling et al. | |
| 6,213,986 B1 | * | 4/2001 | Darling, Jr. | 604/248 |

OTHER PUBLICATIONS

3M Health Care brochure Copyright date 1993.

* cited by examiner

*Primary Examiner*—Nicholas D. Lucchesi
*Assistant Examiner*—Christopher D Koharski
(74) *Attorney, Agent, or Firm*—Kinney & Lange, P.A.

(57) ABSTRACT

A pressure compensating IV rate flow regulator having a housing with a metering port and an outlet. The flow rate is set by adjusting a flexible disk to vary the clearance between a metering port and flow passageway. The controlled fluid passes to a land surrounding the outlet. A flexible control membrane having specific design and material characteristics extends across the land and will move or oscillate away or towards the outlet port in response to changes in head pressure, venous back pressure or patient movement. The resulting oscillation of the membrane serves to maintain the flow rate originally set by the clinician. The regulator is provided with safety and operational convenience features such as tactile indicators for "off" and KVO settings and has provision for use with accessory items such as a pole mount holder or anchoring device secured at the forearm or chest.

24 Claims, 9 Drawing Sheets

PRESSURE COMPENSATING IV FLOW CONTROL REGULATOR

CROSS REFERENCE TO PREVIOUS APPLICATION

This application is based on provisional patent application Ser. No. 60/349,834, filed Jan. 16, 2002, entitled "Pressure Compensated Flow Regulator."

FIELD OF THE INVENTION

The present invention relates to a device for regulating and controlling the flow of intravenous solutions to a patient in a gravity infusion system. More particularly, the present invention relates to a disposable, single-use, gravity-flow regulator which is adjustable to closely maintain a pre-set flow rate independent of pressure change due to changes in elevation of the fluid container, venous backpressure or patient movement.

BACKGROUND OF THE INVENTION

Gravity administration of fluids by IV infusion, also known as IV therapy, is a widely practiced medical procedure. Drugs and fluids such as blood, plasma, dextrose and isotonic saline solutions are administered to patients in this manner.

In the typical administration set, a container containing the IV solution is provided to the attending medical personnel. The container has a seal which is broken by insertion of a piercing spike on the drip chamber. A flexible tubing line delivers the IV fluid to the patient. The purpose of the drop chamber is to facilitate the determination of flow or drip rate through the tubing. Infusion rates may be regulated by the use of an external pinch valve or roller clamp associated with the tubing for less critical gravity-type infusions.

The procedure involves initially purging the tubing and needle of air by initiating a flow of fluid through the tubing. Once this is done, the needle is then inserted into the venipuncture site, such as a location in the forearm or wrist of the patient, and fluid flow is initiated. Medical personnel will normally adjust a pinch valve or roller clamp to restrict the IV tubing. The number of drops passing through the drip chamber is visually counted or timed. The appropriate flow rate is established by trial and error by progressively restricting or opening the lumen in the tubing using the pinch valve or roller clamp. Roller clamps and pinch valves compress the delivery tubing and are not very accurate as they deform the tubing due to the physical properties of the tubing, the inner diameter may change during use.

The administration procedure described above requires the attention of medical personnel for a substantial period of time. However, once a drop rate is set, the rate can be subject to substantial deviation as a result of a number of factors. As the administration of the IV progresses, the fluid level within the solution container will lower, reducing the effective head pressure, causing the drop rate to reduce. The drop rate may also be significantly affected by a change in the elevation of the container or by movement of the patient. Accordingly, the traditional clamping procedures are subject to error and deviation and may deliver fluid at too low or too high a rate which may be adverse to the patient, particularly critical care patients.

Accordingly, various approaches can be found in the prior art to maintaining constant IV flow rates in gravity systems. Flow can be regulated by controlling pressure or resistance either mechanically or electro-mechanically. For example, U.S. Pat. No. 4,343,305 discloses an adjustable rate, constant output infusion set having a connector piece connectable to a container and a headpiece rotatably attached to the connector to adjust the flow rate. An elastically stretchable diaphragm is interposed between the connector piece and the head piece. The connector piece forms a first chamber with a diaphragm which is in direct communication with the container by an inlet port. The headpiece forms a second chamber with a diaphragm, which is in communication with the patient by a control board. The headpiece is rotatably attached to the connector to adjust the flow rate. A passageway connects the first chamber and the second chamber and the diaphragm and by virtue of elasticity maintains a constant pressure drop between the chambers so that the fluid passes the control port at a constant rate of flow.

U.S. Pat. No. 4,515,588 shows a flow regulator for use in an IV administration arrangement which establishes and maintains the rate of flow regardless of changes of pressure. The regulator utilizes a diaphragm control orifice and bypass with a valve to establish the flow rate. The diaphragm adjusts the effective orifice opening to maintain the constant flow selected by the valve setting.

U.S. Pat. No. 4,769,012 discloses a flow regulating device for gravity infusion and transfusion of fluids which has an upper and lower housing and having inlet and outlet channels respectively. A continuously adjustable valve is connected between the inflow and outflow channels. The outflow channel has an outlet opening which defines a valve seat and a a membrane extends across the outlet opening and is movable toward and away from the outlet opening, depending on pressure occurring on opposite sides of the membrane. In this way, extraneous factors such as patient venous pressure can be compensated by the membrane to maintain substantially constant flow of fluid once the valve is set.

U.S. Pat. No. 5,240,035 discloses a pressure compensator for maintaining essentially constant flow rates in an IV system having a source of IV fluid and a controller. The compensator is connectable to the controller and has a housing with a flexible membrane extending transversely therein defining opposite control chambers. One control chamber communicates with the source of IV fluid and also connects to the inlet of the flow controller. The second control chamber receives the regulated flow from the control valve. The second control chamber is generally conical or convex, sloping to an outlet port which is connected to the tubing line leading to the patient. The outlet from the second chamber is smaller than the inlet to the second chamber and the diaphragm serves to control flow to the patient by compensating for pressure changes, such as change in fluid head. The configuration of the second chamber and the configuration of the outlet in the second chamber minimize air entrapment and provide greater flow capacity.

While devices of the type described above improve accuracy in IV delivery systems, there nevertheless exists a need for a cost-effective, reliable, accurate and effective IV regulator which will maintain a substantially constant flow of IV fluid once a flow rate is set. There further exists a need for a device which requires minimal manipulation so that when the regulator is placed in use in an IV administration system, the requirement for drop counting and readjustment is either minimized or eliminated.

BRIEF SUMMARY OF THE INVENTION

Briefly, the present invention provides a gravity flow rate regulator for administering IV solutions. The regulator is connectable to a line leading to the IV fluid container at a tubing connector. The solution container is supported in a position above the venipuncture site so that fluid will flow by means of gravity through the tubing to the venipuncture site. The regulator is adapted to be interposed in the tubing line between the IV solution container and patient.

The regulator has a housing which supports a flexible membrane interposed between an inlet and outlet, establishing inlet and outlet chambers. Fluid from the IV container enters the housing through an inlet port which, in one embodiment, is disposed at an angle with respect to the regulator body. As the fluid flows through the regulator to the outlet it passes across a metering port and into an outlet chamber surrounding the outlet. The outlet chamber has a raised land or annular rim surrounding an orifice opening into the outlet. A flexible membrane is disposed across the land so that flexing or oscillating of the membrane toward or away from the orifice will control the flow of liquid through the outlet orifice. The membrane is subject to outlet pressure against its lower surface and to inlet or head pressure against its opposite upper surface. The pressure differential across the membrane operates to maintain the preset flow through the outlet by oscillating to adjust the effective opening of the orifice to compensate for changes in fluid pressure.

A valving device such as a screw attached to a large control dial provides precise control so the medical attendant may easily and accurately establish the rate of flow through the metering port by progressively advancing or retracting an elastomeric disk with respect to a flow passage in the fluid flow path in the regulator.

The control dial for manually setting the flow rate is provided with a detent that provides a tactile indication of settings such as KVO (keep vein open), an "off" or locking position as well as providing a stop at the full flow position. The dial is further provided with a safety lock to prevent inadvertent or unauthorized changing of the dial setting once it is set. The dial has spaced grooves extending around the dial engaging a fixed projection so that the user is provided tactile feedback as the dial is manually rotated between settings.

The regulator membrane and metering disk are selected having specific characteristics to ensure accuracy. Other features of the regulator include internal sealing to minimize leakage and a large radius outlet port for debubbling. In an alternate embodiment, the inlet port extends through an arcuate slot in the dial so a large, manually adjustable dial may be utilized. The regulator may be used with various types of IV fluids, even high viscosity fluids and lipids.

BRIEF DESCRIPTION OF THE DRAWINGS

The above and other objects and advantages of the present invention will become more apparent from the following descriptions, claims and drawings in which:

DETAILED DESCRIPTION OF THE DRAWINGS

Figure 1:
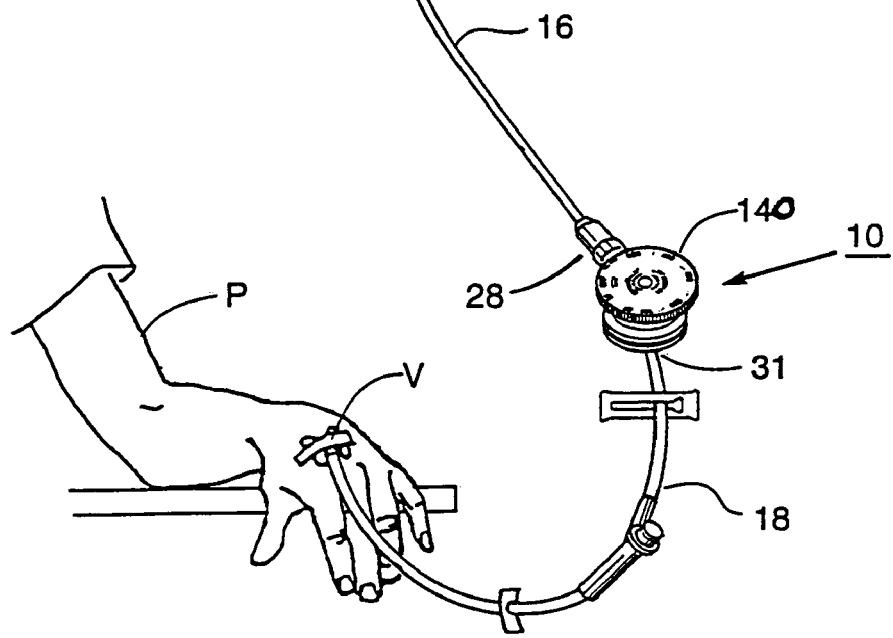
FIG. 1 is a schematic view of a representative IV administration system incorporating the flow control regulator of the present invention.

Turning now to the drawings, particularly FIGS. 1 to 9, an embodiment of the pressure compensated flow control regulator of the present invention is shown and generally designated by the numeral 10. The flow control regulator 10 is a gravity-flow regulator and preferably is a disposable, single-use device provided to the user in a sterilized package. Gravity devices rely on fluid head pressure to overcome the back pressure of the patient's venous system. As seen in FIG. 1, in use the regulator 10 is interposed at a location between an IV fluid source 12 and the patient P. The flow regulator is connected to tubing line 16 which leads to an IV drip chamber 15 inserted into an IV fluid source 12 at a piercing spike. It is customary to locate the flow control regulator at an intermediate elevation below the level of the IV fluid.

The outlet of the flow control regulator 10 is connected to flexible tubing line 18 which leads to the patient and terminates at an administration needle at the venipuncture site "V." As discussed above, one problem with non-compensated flow control devices is that changes in head pressure due to changes in the fluid level within the IV container, changes in elevation of the fluid container on the IV stand or movement of the patient's limb can adversely affect flow control rates. The major determination of pressure in gravity administration systems is head height which refers to the distance between the fluid level in the IV solution container and the IV site "V."

In conventional systems, a roller clamp may be interposed between the IV source and the regulator. In such systems, the roller clamp is used to establish a drop rate by counting drops. However, with the regulator of the present invention, use of a roller clamp is not necessary for adjustment and may be incorporated for use only when initiating or stopping flow.

The flow control regulator 10 has a housing or body 24 consisting of components including an upper housing 36, an intermediate or middle housing 28 and lower housing 31. These housing components are preferably fabricated by injection molding using a suitable medical grade plastic material such as ABS or polypropylene. Although the housing components are shown as separate components for ease of fabrication and assembly, they may be unitary.

Housing 28 has an inlet port 32 which defines an inlet passage 29. The inlet port 32 is generally cylindrical and is sized to be connectable to conventional medical tubing 16.

The inlet port 32 is preferably disposed at an angle greater than 45° with respect to the vertical axis of the regulator and may extend to 90°. The angular orientation of the inlet port 32 provides significant functional advantages in that the angular orientation facilitates use of an easy-to-adjust dial 140 having a large diameter. The angular orientation of the inlet port also allows the regulator to hang in a suspended, in-line position with the surface of dial 140 in a vertical or near vertical, easy-to-read position, as seen in FIG. 1.

Figure 10:
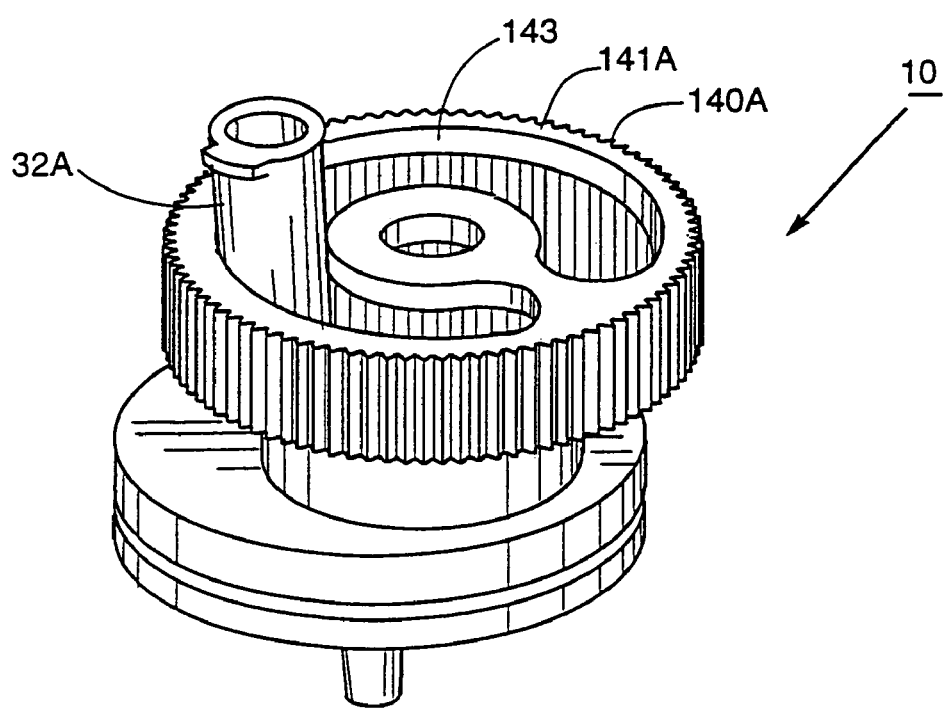
FIG. 10 is a perspective view illustrating another configuration of the regulator body.

FIG. 10 shows the regulator 10 with a large circular dial 140A which operates as has been described. To accommodate the large diameter dial 140A, the surface 141A is provided with an arcuate groove 143. This allows the inlet 32A to extend axially through the slot 143.

Circular wall surface 34 is provided with a concentric, downwardly depending circular flange 40 which engages the lower housing 31. An annular flange 46 extends upwardly from the upper surface 34 at a location offset from its center. At the center of the top surface area defined by the upper flange 46 is a vertically extending orifice 50 which has a generously radiused upper edge 51 which transitions to the top surface of the wall. A small annular sealing ridge 52 on the upper surface of wall 34 extends adjacent the flange 46.

Figure 2:
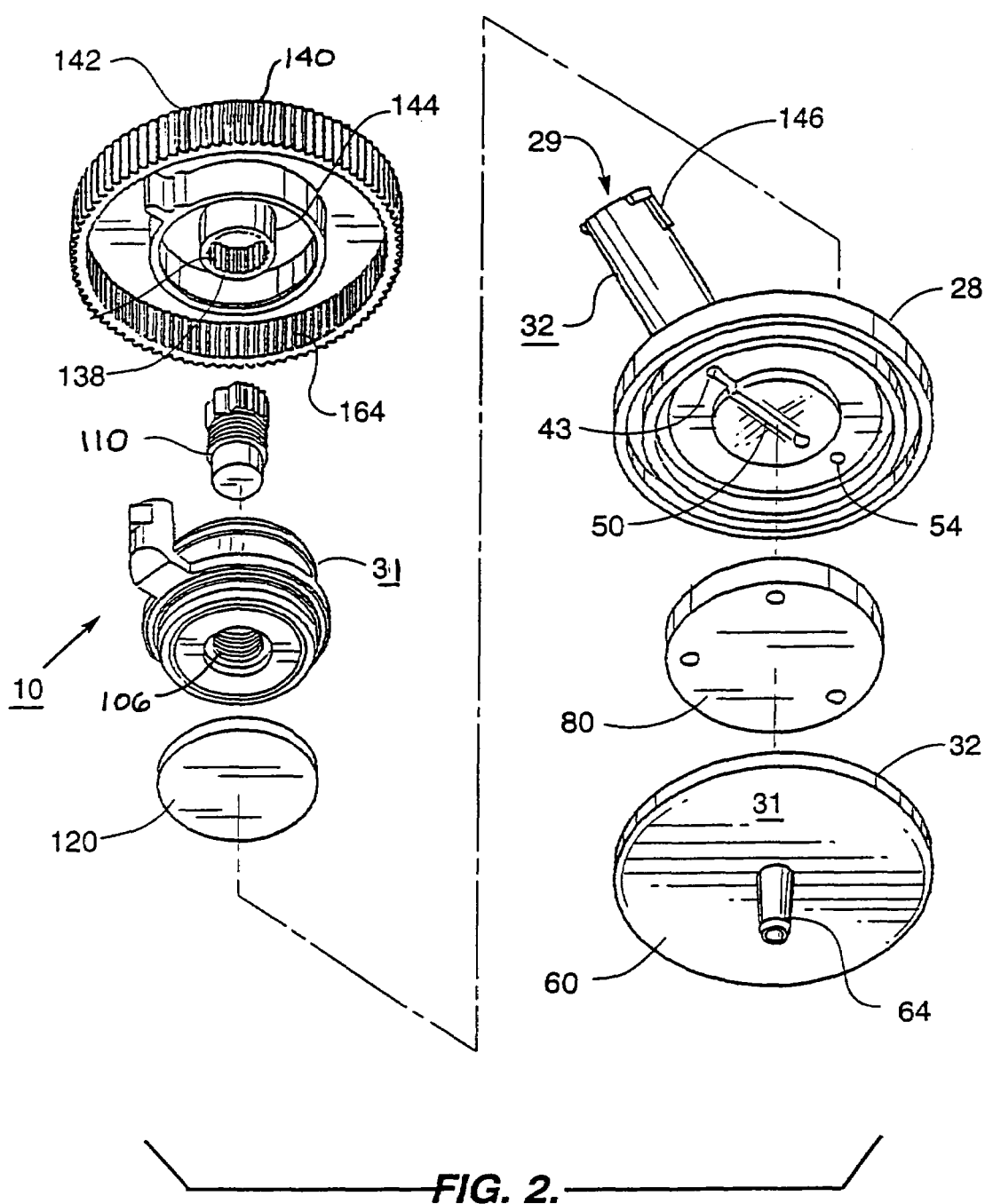
FIG. 2 is a bottom exploded view of the flow regulator of the present invention.
Figure 3:
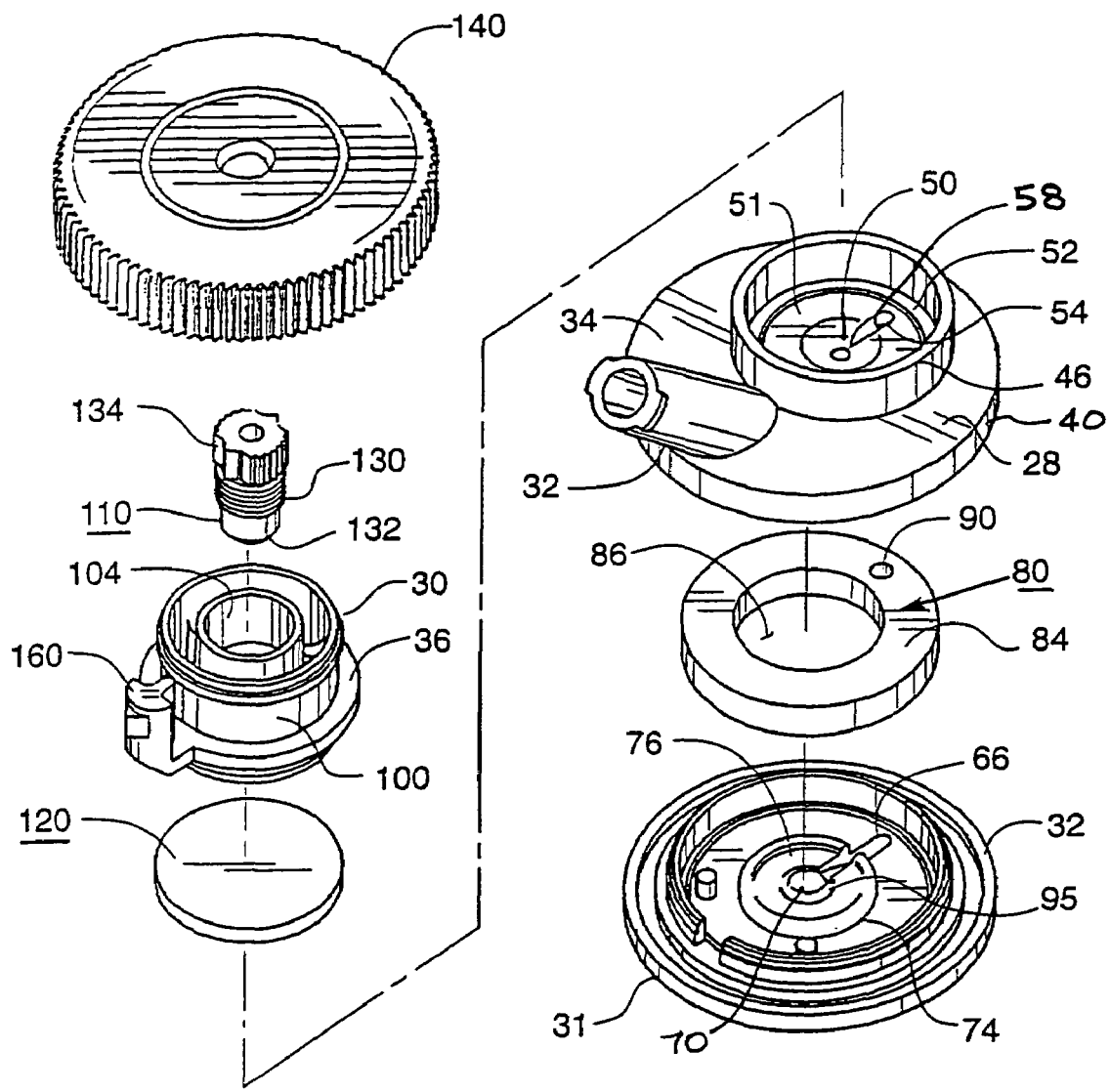
FIG. 3 is a top exploded view of the flow regulator of the present invention.
Figure 5:
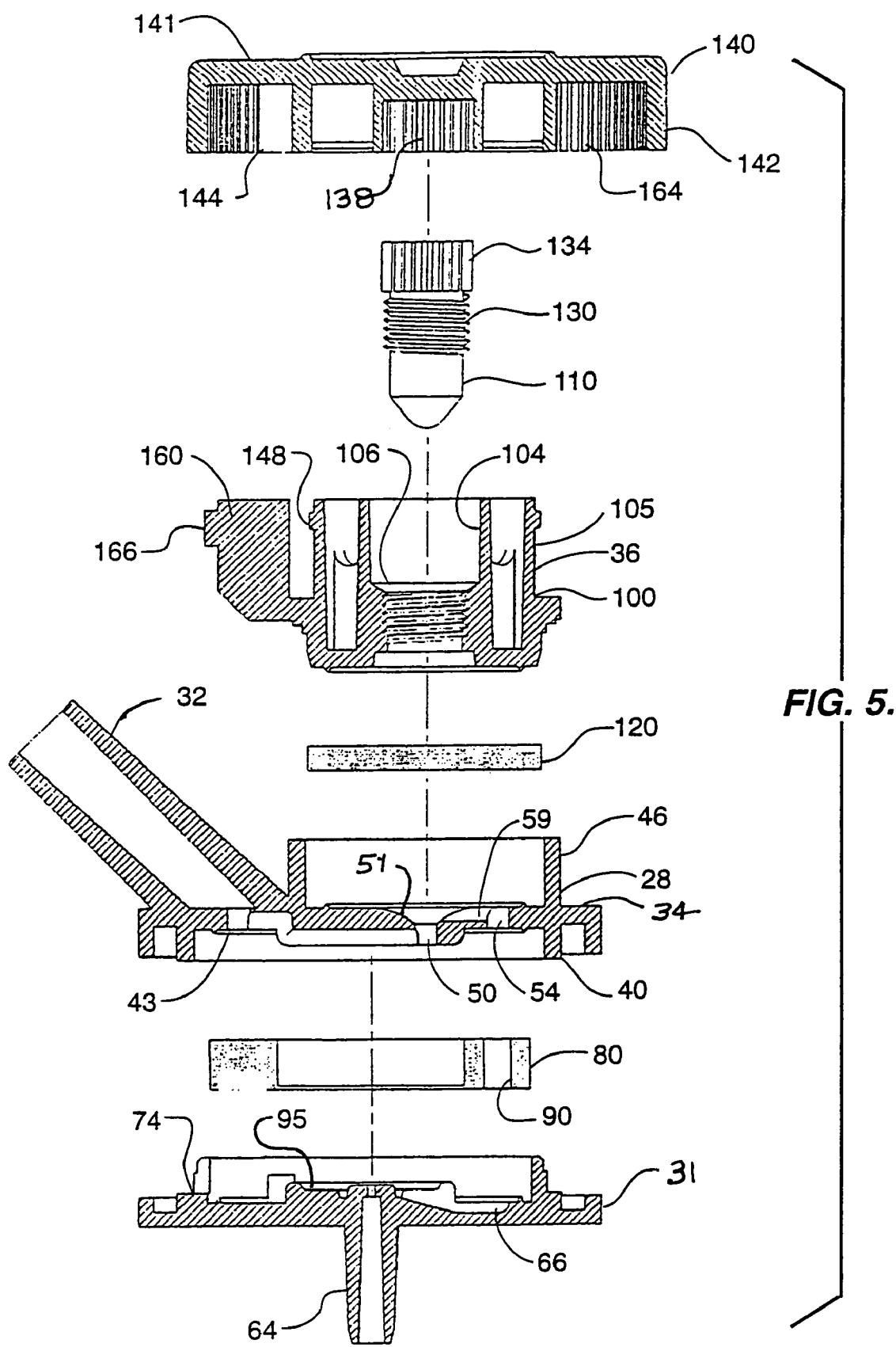
FIG. 5 is an exploded vertical cross-sectional view of the regulator.
Figure 6:
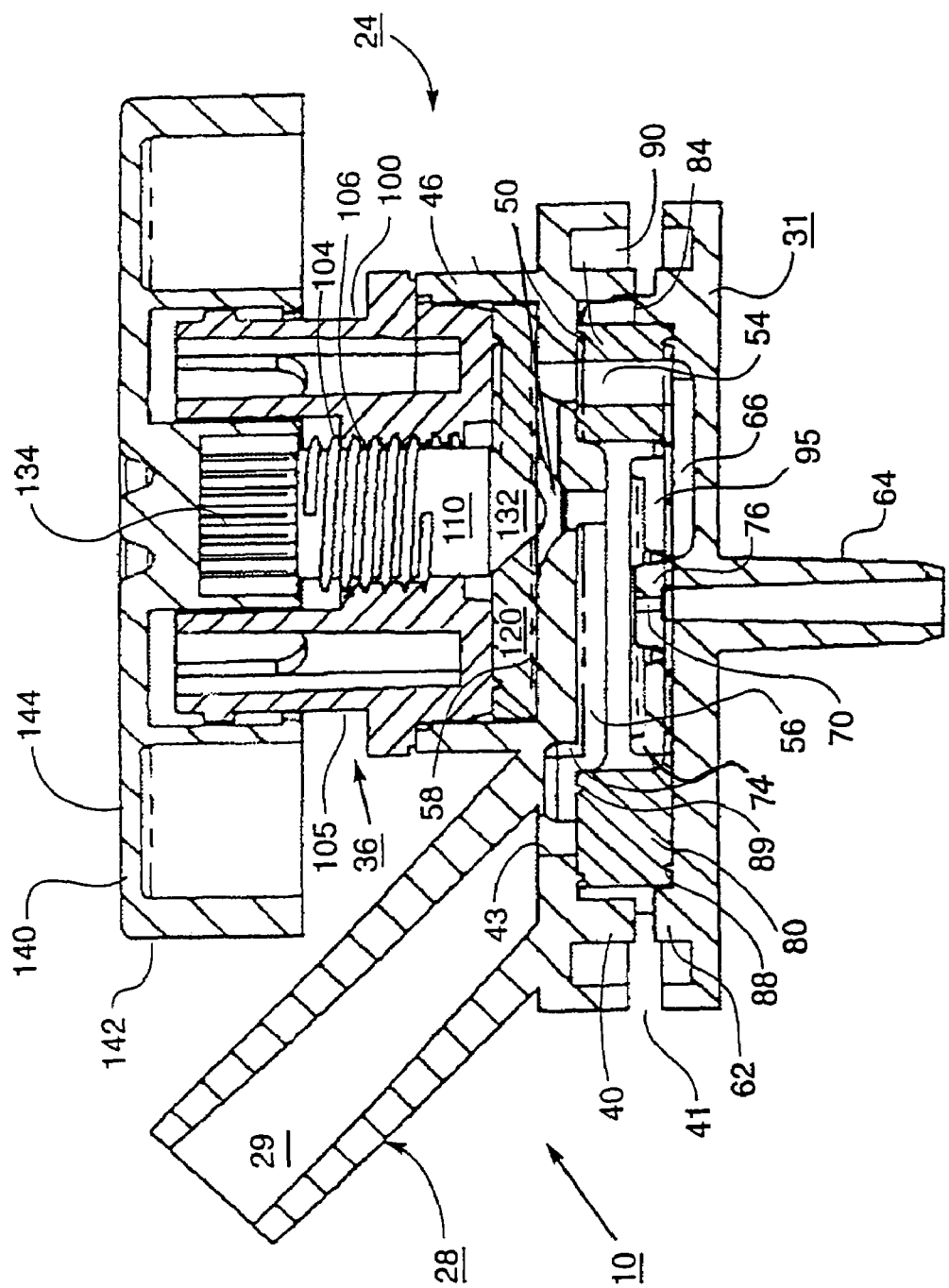
FIG. 6 is an enlarged cross-sectional view of the regulator.

A second orifice 43 is provided in wall surface 34 at the lower end of the inlet passage 29. A shallow groove 56 extending in the bottom of wall 34 communicates orifice 43 with the center orifice 50. A radial flow passageway 58 along the top of wall 34 extends between the center orifice 50 and orifice 54. Orifice 54 extends through wall 34 radially spaced from center orifice 50. These passageways are best seen in FIGS. 2 and 3.

The lower housing 31 has a generally circular planar bottom surface 60 with an upstanding peripheral flange 62 which, in the assembled position, engages the depending flange 40 of the middle housing. An outlet fitting 64 depends at a central location from the outlet housing. The fitting 64 is sized to accommodate attachment of conventional medical tubing 18 which leads to the patient. The outlet fitting 64 is spaced or offset from the location of orifice 54 located in the middle housing.

The upper surface of the lower housing wall defines a radially extending passageway 66 which, when the components are assembled, is aligned with orifice 54. An outlet orifice 70 extends through the bottom wall and is centered within an annular flange 74. The orifice is located in a raised, circular land 76 which surrounds the outlet orifice 70.

Figure 11A:
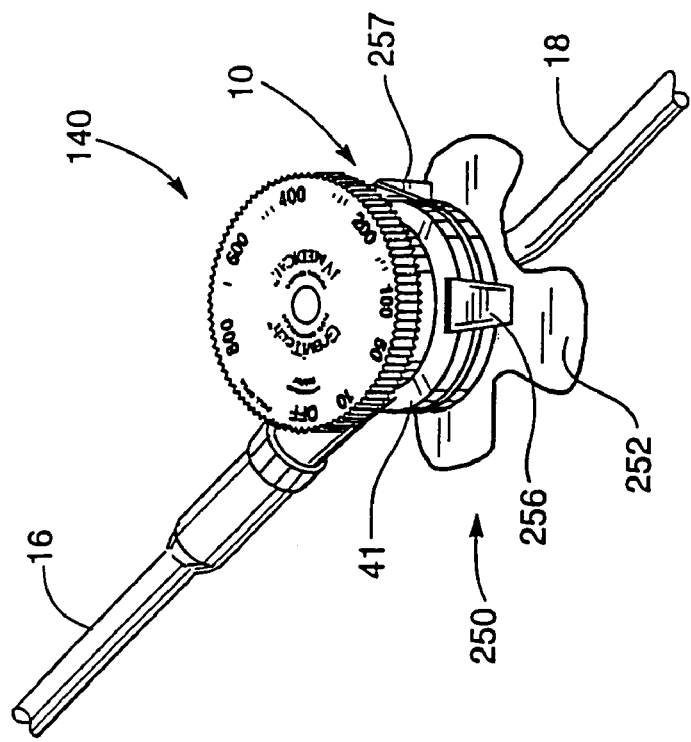
FIG. 11A shows the regulator of the invention attached to a securement device, the securement device being securable to the chest or forearm of the patient.
Figure 11:
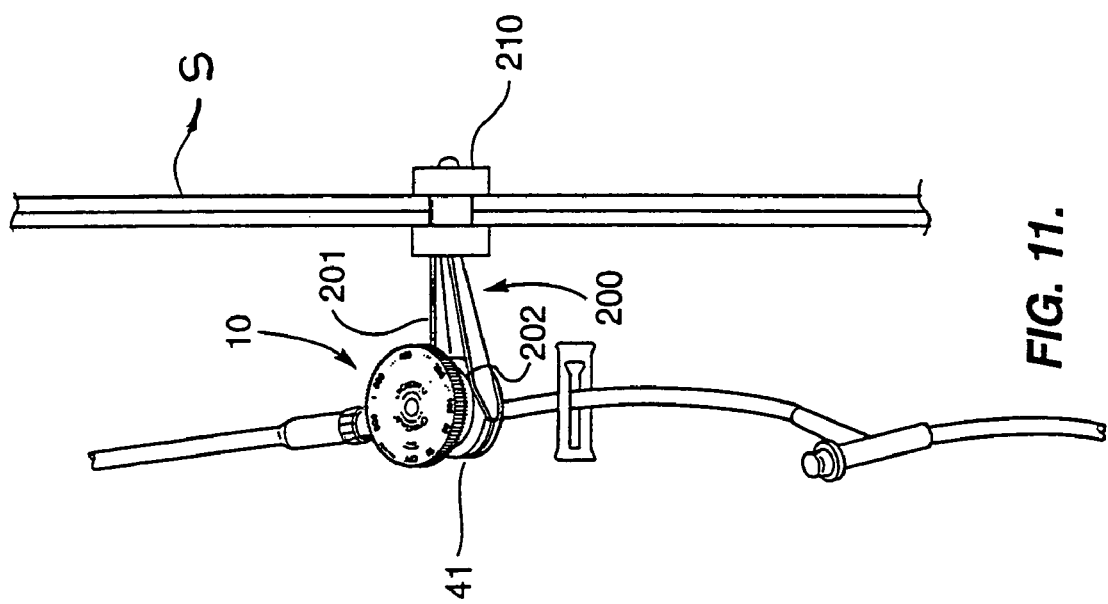
FIG. 11 shows the regulator attached to an accessory pole mount holder by an anchoring or securement device.

The peripheral outer edges of the upper housing and the lower housing define a peripheral groove 41 about the regulator body. The groove 41 accommodates temporary attachment of the regulator 10 to an accessory such as a pole mount holder or a patient anchoring device such as safety securement device, as seen in FIGS. 11 and 11A. The device 10 is securable to a support pole S by securement device 200 and having arms 201, 202 engageable in groove 41. The regulator may be easily "snapped" in place with the arms of the holder engaging the groove 41. The securement device has a clamp 210 adjustably attachable to the pole S. In FIG. 11A, the regulator 10 is shown with a patient securement device 250 which has a base 252 adhesively securable to the patient. The base 252 has a plurality of projections 256, 257 which releasibly engage the body of the regulator along peripheral groove 41.

An elastomeric membrane 80 is seated within chamber 82 defined by the upper surface of the lower housing and with the lower surface of the middle housing. The elastomeric membrane 80 is of a suitable medical grade material such as silicone rubber. The membrane has characteristics critical to the performance of the regulator and the maintenance of accurate flow rates once set by the clinician. The membrane flexes or oscillates to regulate flow to compensate for pressure changes as described above. The elastomeric membrane has a generally annular outer flange 84. A thin, flexible center section 86 extends across the inner edges of the annular section. Typically, the thin, flexible center section of the membrane will have a thickness within the range of 0.0125" to 0.0175." The membrane is best seen in FIG. 3.

It has been found that a thinner membrane will generally provide greater accuracy at lower head height and less accuracy as head height increases. It has been found that an optimal thickness for the flexible section of the membrane is about 0.015".

In the assembled position, the central membrane flexible section 86 extends across top of land 76 and across outlet orifice 70. Small annular sealing projections or ridges 88, 89 extend from the surfaces of the lower housing and upper housings positioned to sealingly engage the opposite surface of membrane flange 84 to prevent fluid leakage around the edges of the membrane. The characteristics of the membrane 80 are critical to proper operation. A membrane fabricated in accordance with the following has been found to work well providing the necessary control and accuracy.

The membrane is preferably fabricated by compression molding using a silicone material having the following characteristics listed below:

| MEMBRANE MATERIAL CHARACTERISTICS | | |
|---|---|---|
| Durometer, Shore A | 50 and above | ASTM D2240 |
| Tensile Strength | 1100 to 1200 | ASTM D-412 |
| Elongation % | 200 to 300 | ASTM D-412 |
| Modulus @ 100% | 60 to 70 | ASTM D-624 |
| Tear Strength | 50 to 60 | ASTM D-624 |
| Bayshore | 60 and above | ASTM D-624 |

Figure 9:
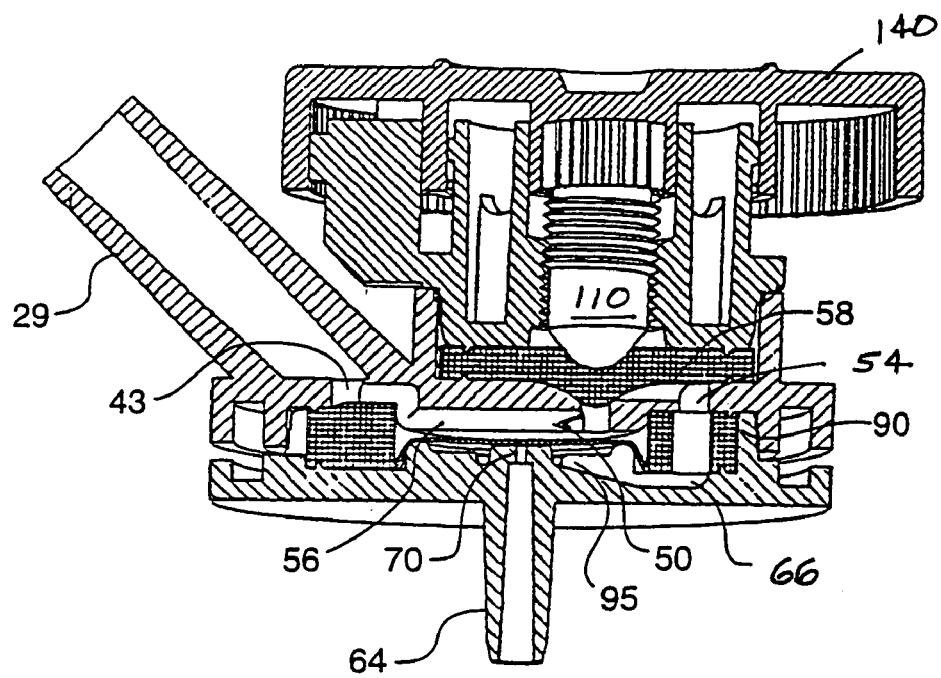
FIG. 9 is a schematic diagram illustrating the flow path through the regulator.

A vertical port 90 is provided in the annular portion 84 of the membrane and, when the regulator is assembled, aligns with the orifice 54 in the inlet housing and communicates this passageway with the radially extending groove 66 in the upper surface of the bottom housing. Thus, as seen in FIG. 9, a flow path is established from the inlet passageway 29 through the orifice 43 at the bottom of the inlet passage and extending radially along channel 56 to central orifice 50 in the middle housing. The flow path continues upwardly through orifice 50 and then radially along channel 58 to a location registering with the vertical port 90 in the annular portion of the membrane 80. Fluid will then flow downwardly through the port 90 to the radial passage 66 in the lower housing. Fluid will then pass between the membrane and the bottom surface to an annular outlet chamber 95. This chamber 95 is defined by annular ring 74. Raised land 76 is located in the center of ring 74 and defines an outlet orifice 70 communicating with the lumen in the outlet fitting 64.

The flow control regulator further includes an upper housing 36. The upper housing 36 has a generally cylindrical body 100 which, when assembled, is received within the annular flange 46 of the middle housing 28. The upper housing 36 defines a vertical bore 104 which is aligned with an orifice in the middle housing. Bore 104 defines the plurality of screw threads 106 which are preferably left hand threads. An elastomeric flow control disk 120 is seated on the upper surface of the middle housing extending across the upper end of the orifice 50. An adjusting screw 110 is threadably received in the threaded bore 104. The adjusting screw has a body with external male threads 130 which are engageable with the threads 106 in the upper housing.

The pitch of the mating screw threads 106 and 130 are selected to provide ease of adjustment and to spread the range of adjustment over about 360° of dial rotation. A thread pitch of about 48 has been found to work well providing medical technicians "feel" for the precise adjustment. The lower end of the screw body tapers to a rounded point 132 which engages the upper surface of the elastomeric disk 120.

The disk 120 is preferably molded silicon having a thickness approximately 0.070". The preferred material characteristics for the control disk are set forth in the above Material Characteristic chart below.

CONTROL DISK MATERIAL CHARACTERISTICS

| Test Method Description | Unit | Lower Unit | Upper Unit |
|---|---|---|---|
| COMPRESSION SET 22/350F A/B BLEND PB | % | 0 | 35 |
| DUROMETER A/B BLEND PB | No Unit | 57 | 65 |
| ELONGATION A/B BLEND PB | % | 320 | 550 |
| MODULUS 100% PSI A/B BLEND PB | psi | 0 | 900 |
| TENSILE PSI A/B BLEND PB | psi | 1159 | 2000 |
| TEAR B PPI A/B BLEND PB | ppi | 143 | 400 |
| SPECIFIC GRAVITY DENSITRON ASTM792-A | No Unit | 1.11 | 1.15 |
| GOETTFERT T90 MINUTES | min | 4.5 | 6.5 |
| GOETTFERT RHEOMETER C.I.T. LINEAR PRG. | ° C. | 113.0 | 120.0 |

Figure 12:
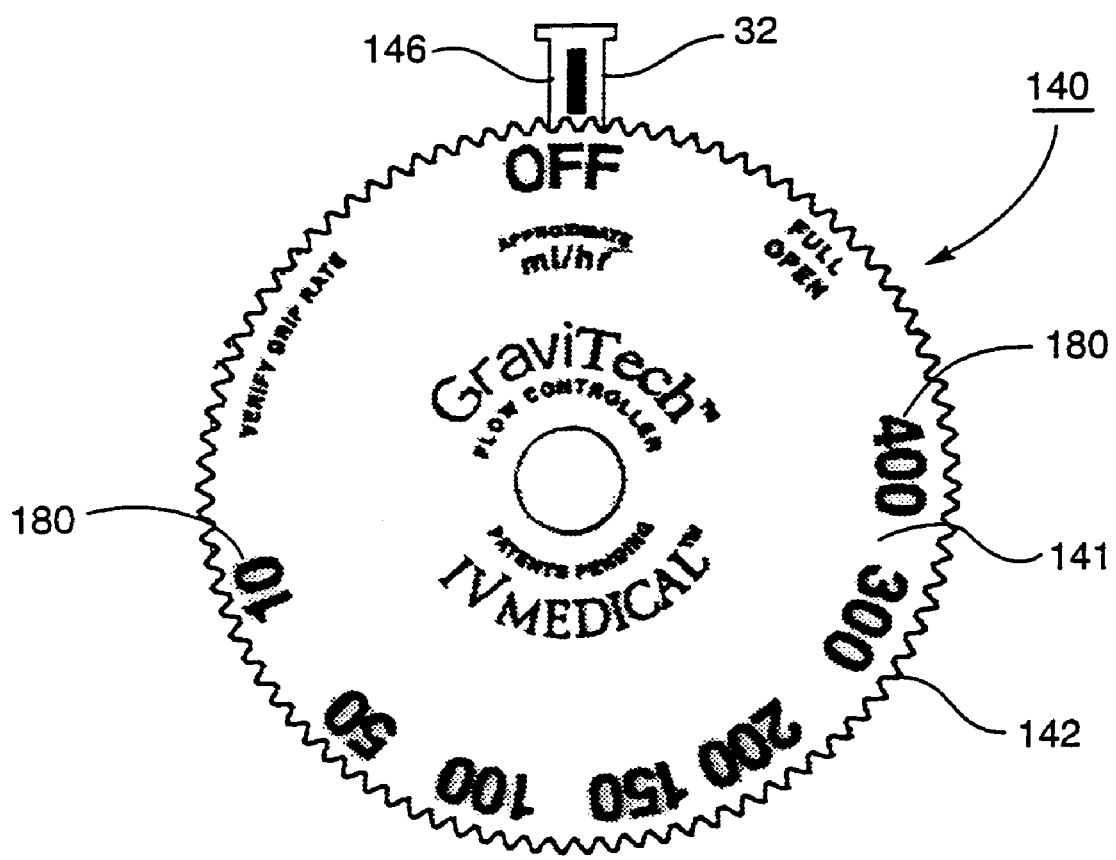
FIG. 12 shows the top surface of the dial.

The upper end of the screw 110 has a plurality of axial ribs 134 which are received within the cooperating opening 138 in the control dial 140. The control dial 140 has an upper generally planar surface 141 which has a substantial diameter for ease of use and which may be provided with flow rate indicia graduations 180 from 0 to full flow which are positioned relative to the screw when the regulator is calibrated, as seen in FIG. 12. The graduations are indexed with reference to indicator 146 located on the inlet 32 as best seen in FIG. 12. The outer edge of the control dial forms a downwardly depending surface 142 which may be ribbed or knurled on its exterior for ease of use. An inner, annular flange 144 closely cooperates with the smooth, outer surface 105 of the housing 36 having cooperating grooves 148 so the dial may be "snapped" in place over the upper end of the screw and secured to the screw in a desired calibration position at assembly with respect to the upper housing and disk 120.

It will be apparent that by rotating the control dial, rotation will also be imparted to the adjusting screw 110. As the adjusting screw is advanced by rotating the dial in a counterclockwise direction, the elastomeric disk 120 will be forced downwardly toward the upper radiused edge 51 of the control orifice 50 reducing the clearance between the orifice 50 and passageway 59 to reduce the flow rate. Rotation of the control dial in the opposite direction will open the clearance at the control orifice permitting greater flow rate. The upper housing 36 carries flow rate indicia 180 which cooperates with indicator 146 along the center portion of the inlet port 32. The graduations 180 on the upper surface 141 of the control dial indicate flow regulating positions, full off, full flow and purge positions and with intermediate flow rate or graduations indicated between these positions. The flow control regulator is calibrated at the time of assembly as will be explained hereafter.

Figure 4:
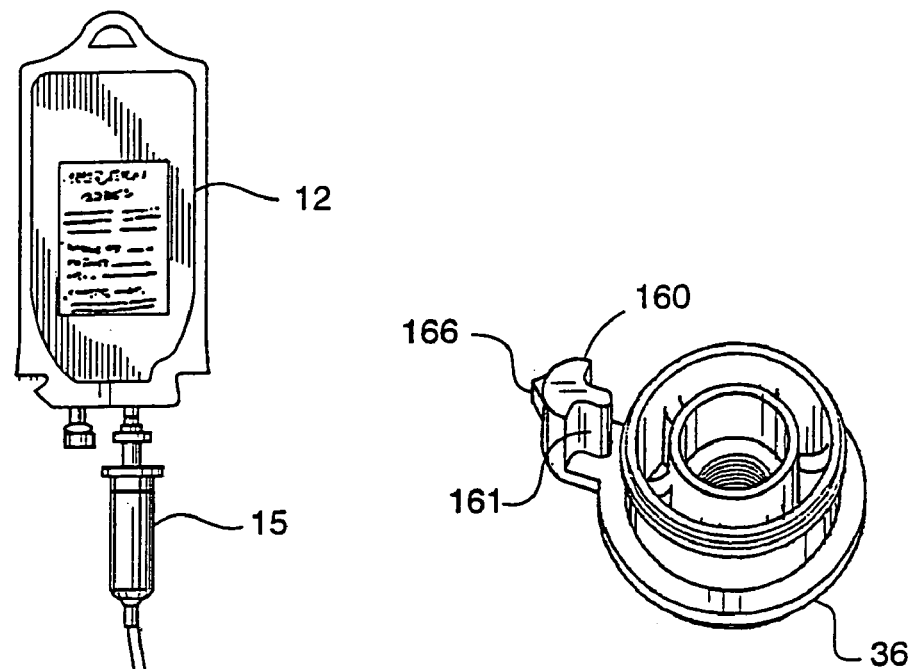
FIG. 4 is a perspective view of the screw housing.
Figure 7:
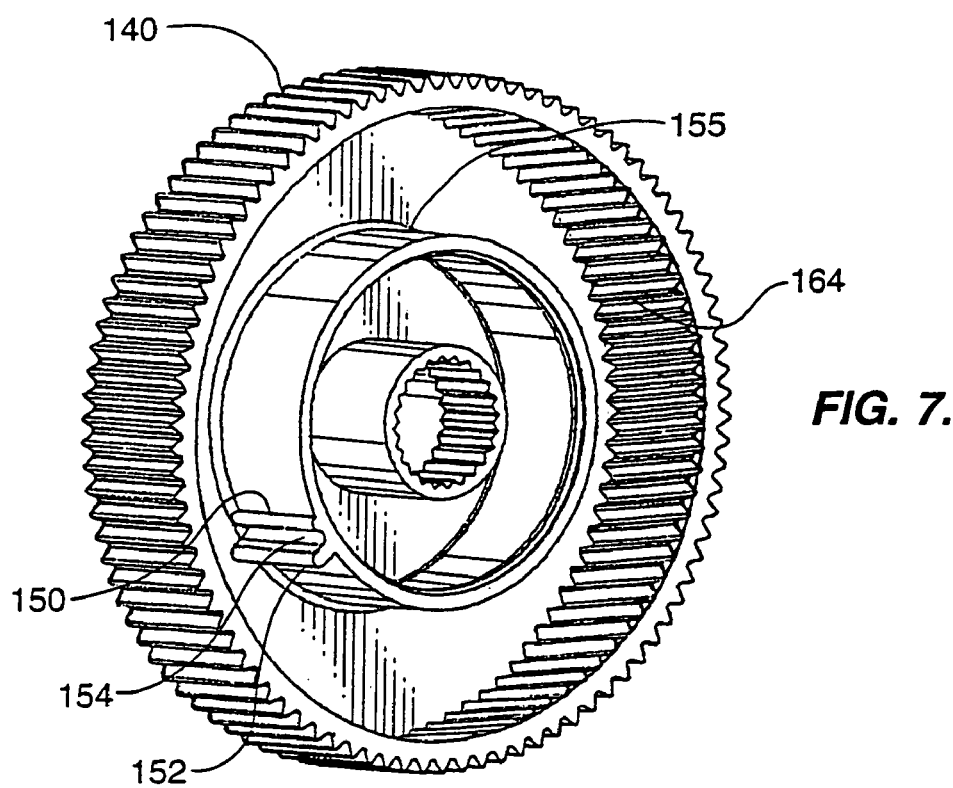
FIG. 7 is a perspective view of the dial showing detent which provides a tactile indication and retention of the "off" position.
Figure 8:
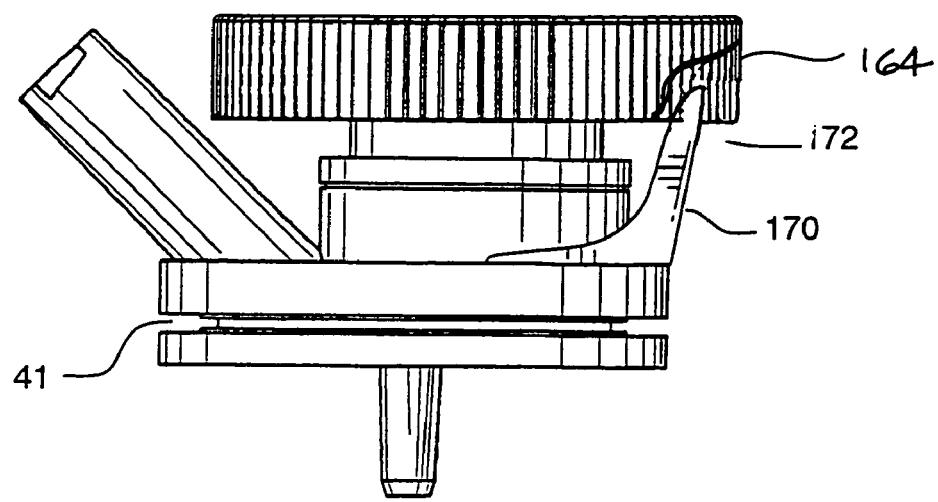
FIG. 8 shows the dial safety lock position preventing inadvertent positioning of the dial.

Referring to FIGS. 4, 7 and 8, several safety features are shown. The control dial 140 may be rotated approximately 360° from "off" to a full open or purge position. In order to provide a positive indication of the "off" position so that a low rate of fluid flow is not inadvertently delivered to the patient, the dial is provided with a detent feature. As seen in FIGS. 4 and 7, a circular flange 155 on the underside of the dial is provided with two adjacent projecting ridges 150, 152 connected by a land area 154. Ridge 150 is shallower than ridge 152. A stop 160 is provided on the housing 36 at the "off" position and has a detent 161 located to be engageable with the ridges. When the dial is rotated counterclockwise to the "off" position, the first ridge 150 will encounter the detent 161 and the stop indicating a slow or KVO position has been reached. Further rotation of the dial will cause the detent 161 to pass over ridge 150 seating in the land 154 in a positive "off." The dial material will deflect slightly. This feature also prevents continued rotation of the dial to prevent it from being removed. Rotation in the opposite direction will cause the detent to abut the ridge 152 in the full open position.

The user is provided tactile input as the dial is rotated to enhance and refine the adjustment procedure. The inner surface of the peripheral dial flange is provided with spaced grooves 164. The stop 160 carries a V-shaped projection 166 which engages the grooves when the dial is assembled. The engagement is a light, frictional engagement so that as the dial is rotated, the user will sense the "click" as the projection 166 rides over the dial surface seating in each groove. The engagement will also assist in preventing inadvertent rotation of the dial caused by incidental contact.

FIG. 8 illustrates another feature which provides a safety lock to prevent inadvertent movement of the dial. A deflectable lever 170 extends upwardly from the middle housing 28 having an upper end with a detent 172 engageable in grooves 164 to prevent dial rotation. The frictional engagement, which is greater than the engagement between projection 166 and grooves 164, will serve to maintain a dial setting even if the dial is attempted to be rotated. The medical attendant must apply an inward force to the lever 170 while holding the regulator body to disengage the detent 172 from the groove in which it is seated. The dial setting can then be changed using the other hand. Release of the pressure applied to the lever 170 will cause it to return to a position engaging the inner grooves 164 on the dial and again locking the dial in the set position.

Operation

In the operation of the flow regulator, a roller or slide clamp, if used, is placed in a closed position and the flow regulator is placed in the tubing line at a convenient location between the drip chamber and the administration needle, as seen in FIG. 1. The flow regulator needs to be positioned below the fluid level of the container as the device is gravity-driven. Conventional connectors and adaptors are conventionally used and are employed to make the connection.

Air is purged from the system by opening the flow regulator to the full open or purge position as indicated by the indicia on the control dial 140 and disengaging the roller clamp/slide clamp. Once the air is purged from the system, the control knob is rotated to a position to a fully closed position by turning on the knob to force the disk downwardly. Once a needle is inserted in the venipuncture site "V" the control dial can be rotated to the suitable selected position indicated on the dial to establish a desired flow rate. In some instances it may be desirable to check or confirm the flow rate by timing the drop rate through the drip chamber. The medical clinician will confirm the flow rate by timing the drop rate through the drip chamber.

Once the device is set at the desired flow rate, the control membrane 80 will function and maintain an essentially constant flow rate regardless of changes in fluid level within the IV container or patient movement. As indicated, flow will pass from the inlet across the middle housing to the rate control orifice 50. The position of the screw 110 will determine the position of the elastomeric disk 120 relative to the orifice 50 and the radial passageway 58 of the middle housing 28 controlling the rate of flow passing passing through the aperture and radially to the passageway in the membrane. Fluid will then pass downwardly and radially through the passageway in the upper surface of the lower outlet housing and will enter the orifice at the upper end of the outlet. The opening or space between the orifice and lower surface of the flexible membrane will vary in response to pressure in the chambers or either side of the thin membrane. It will be appreciated that the upper surface of the flexible membrane is subjected essentially to the pressure existing in the inlet. The pressure existing at the underside of the membrane at the outlet orifice is the pressure existing at the venipuncture site.

If the pressure within the inlet chamber is reduced due to a decrease in head pressure or patient movement towards the fluid source the resulting reduction in inlet pressure relative to outlet pressure will force the membrane away from surface 76 of the land to effectively increase the orifice opening to the outlet passageway with a compensating increase in flow. Conversely, by increasing the elevation of the IV fluid container, head pressure will increase and similarly have an opposite effect by forcing the elastomeric membrane down on its landing and closer to the outlet port, decreasing the effective orifice opening of the outlet passageway with a compensating decrease in flow.

Calibration

Calibration is accomplished by connecting the inlet to a source of static fluid pressure (air or liquid). The dial has not been assembled and the screw 110 is used to turn the regulator to an "off" position. The regulator is tested for leakage by observation and by pressure readings on a pressure gauge. Calibration is generally performed with reference to a head height of 32" which is representative of most IV set-ups.

After leak testing, the dial 140 may be affixed to the adjusting screw by aligning the proper dial indicia "off" with the "off" position of the screw. The dial is then rotated to the full open position so that the disk is not subject to pressure from the screw tip 132 that may deform it. The unit may be packaged and subject to sterilization by gas or gamma ray as is conventional.

It will be obvious to those skilled in the art to make various changes, alterations and modifications to the invention described herein. To the extent these various changes, alterations and modifications do not depart from the spirit and scope of the appended claims, they are intended to be encompassed therein.

I claim:
1. An IV rate flow regulator comprising:
(a) a housing having an inlet and an outlet, said inlet extending upward and outward from the housing and connectable to a source of IV fluid, and an outlet extending downward from the housing and connectable to administration means;
(b) said housing defining a metering orifice;
(c) flow control member extending across said metering orifice;
(d) control means cooperable with said flow control member to establish a predetermined rate of flow through said metering orifice to said housing outlet, said control means including a manually rotatable control dial positioned generally above the housing;
(e) an annular land extending around an outlet orifice communicating with the housing outlet;
(f) a membrane responsive to head pressure variations to control the rate of fluid flow through the outlet which substantially maintains said predetermined flow rate, said flexible membrane having an annular flange and a thinner central control section having a thickness approximately between 0.0125" to 0.0175", said thinner control section extending across the area defined by the annular flange; and
(g) an indicator positioned on an outer surface of the inlet and positioned adjacent an outer edge of the dial to cooperate with indicia on the dial to indicate a flow rate setting of the regulator.

2. The IV rate flow regulator of claim 1 wherein said control dial has peripheral notches which cooperate with a detent on the body to provide an audible and tactile feed back to the user as the dial is rotated.

3. The IV rate flow controller of claim 1 wherein said flexible flow control member is a silicone disk fabricated by molding.

4. The IV rate flow regulator of claim 1 wherein said housing defines attachment means for attaching the controller to an accessory.

5. The IV rate flow regulator of claim 1 wherein said housing includes sealing ridges engaging the opposite sides of said annular rim of said membrane.

6. The IV rate flow regulator of claim 1 wherein said housing comprises a separate inlet section, intermediate section and outlet housing sections joined together.

7. The IV rate flow regulator of claim 1 wherein a surface of the dial carries flow rate indicia.

8. The IV rate flow regulator of claim 1 wherein said membrane has a durometer hardness of about 55.

9. An IV rate flow regulator comprising:
(a) a housing defining an axis and having an inlet and an outlet, said outlet extending axially from said housing and said inlet disposed and an acute angle with respect to a plane perpendicular to the axis of the housing, said inlet connectable to a source of IV fluid;
(b) said housing defining a metering orifice having a metering outlet;
(c) a flexible flow control member extending across said metering orifice;
(d) screw means cooperable with said flow control member, said screw being advanceable and retractable to establish a predetermined rate of flow through said metering orifice;
(e) a manually rotatable dial operably connected to said screw means having indicia thereon;
(f) said housing having an annular land extending around an outlet orifice opening into said housing outlet;

(g) a flexible membrane having an annular flange and a thinner central control section having a thickness of approximately 0.0155", said thinner control section disposed across said annular flange to control the rate of fluid flow across the outlet orifice to the housing outlet to substantially maintain said predetermined flow rate as fluid head height pressure varies; and (h) an indicator positioned on an outer surface of the inlet and positioned adjacent an outer edge of the dial to cooperate with the indicia on the dial to indicate a flow rate setting of the regulator.

10. The IV rate flow regulator of claim 9 wherein said body is plastic and said flow control member and said membrane are molded silicone.

11. The IV rate flow regulator of claim 9 wherein said body has sealing ridges engageable with the annulus of the control member.

12. The IV rate flow regulator of claim 9 wherein the screw means has left-handed threads.

13. The IV flow rate regulator of claim 9 wherein said inlet carries a reference marker cooperable with said indicia.

14. The IV flow rate regulator of claim 9 and further comprising:
a stop extending from the housing and engageable with a first ridge carried by the dial to define an off position and a full open position.

15. The IV flow rate regulator of claim 14 and further comprising: a second ridge carried by the dial for engaging the stop to define a KVO position.

16. The IV flow rate regulator of claim 15, wherein the second ridge is shallower than the first ridge and is spaced from the first ridge to define a detent for the stop corresponding to the off position.

17. The IV flow rate regulator of claim 9, wherein the stop is aligned with the indicator.

18. The IV flow rate regulator of claim 9, wherein the screw has a thread pitch that allows the flexible flow member to move from a position blocking the metering orifice to a position in which the metering orifice is unobstructed as the dial moves through approximately 360° from the off position to the fully open position.

19. The IV flow rate regulator of claim 9, wherein the inlet is oriented at an angle of about 45° with respect to the plane perpendicular to the axis of the housing.

20. The IV flow rate regulator of claim 9, wherein the dial has a diameter that is approximately equal to a diameter of the housing.

21. An IV rate flow regulator comprising:
(a) a housing having an inlet and an outlet, said housing inlet connectable to a source of IV fluid and said housing outlet connectable to administration means;
(b) said housing defining a metering orifice having a metering outlet;
(c) a flexible flow control member extending across said metering orifice;
(d) control means including a screw having a thread pitch of about 48, said screw rotatable relative to said flexible flow control member to establish a predetermined rate of flow through said metering orifice directed to said outlet, said control means including a manually rotatable control dial;
(e) said housing outlet communicating with an outlet orifice having a land extending around said outlet orifice;
(f) a flexible membrane disposed across said land responsive to head pressure variations to control the rate of fluid flow across the outlet orifice and to the housing outlet which substantially maintains said predetermined flow rate; and
(g) an indicator positioned on an outer surface of the inlet and positioned adjacent an outer edge of the dial to cooperate with indicia on the dial to indicate a flow setting of the regulator.

22. An IV rate flow regulator comprising:
(a) a housing having separate body sections joined together to form a housing, said housing having a flow inlet and a flow outlet, said flow inlet connectable to a source of IV fluid and the flow outlet connectable to administration means;
(b) said housing defining a metering orifice having a metering outlet;
(c) a flexible flow control member extending across said metering orifice;
(d) control means cooperable with said flexible flow control member to establish a predetermined rate of flow through said metering orifice directed to said flow outlet, said control means including a manually rotatable control dial, said control means having indicia cooperable with a reference marker on said flow inlet;
(e) said housing flow outlet communicating with an outlet orifice having a land extending therearound;
(f) a flexible membrane having an annular flange, said flexible control member being disposed across said land and being responsive to head pressure variations to control the rate of fluid flow across the orifice and to the flow outlet to substantially maintain said predetermined flow rate, said housing having sealing ridges engageable with said annular flange of the flexible membrane; and
(g) an indicator positioned on an outer surface of the inlet and positioned adjacent an outer edge of the dial to cooperate with indicia on the dial to indicate a flow setting of the regulator.

23. An IV flow rate regulator for an IV administration system comprising:
(a) a housing including a generally cylindrical upper body section having a first diameter and a generally cylindrical lower body section having a second diameter greater than the first diameter, the lower body section having a central axis offset from a central axis of said upper body section, each housing section having an outer sidewall, said lower body section having a surface extending outwardly past said upper body section;
(b) a flow outlet extending axially from the lower body section, said flow outlet communicating with an outlet orifice;
(c) a flow inlet connected to said lower body section adjacent to the upper body section, said flow inlet being disposed at an acute angle with respect to the central axis of the upper body section and extending upwardly and outwardly past the sidewall of the upper body section;
(d) said housing defining a metering orifice;
(e) a flexible flow control member extending across said metering orifice;
(f) rotatable regulating means cooperable with said flexible flow control member being advanceable and retractable to establish a selected rate of flow through said metering orifice directed to an outlet orifice at said flow outlet;
(g) a manually rotatable dial operably connected to said rotatable regulating means, said dial being generally circular and extending beyond the sidewall of the upper body section and having a diameter greater than the first diameter of the upper body section, said dial having an upper surface carrying flow indicia;

(h) a flexible membrane having an annular flange and a thinner central control section, said thinner control section disposed across said outlet orifice to control the rate of fluid flow to substantially maintain said selected flow rate independent of head pressure variations in the IV administration system; and (i) an indicator positioned on an outer surface of the inlet and positioned adjacent an outer edge of the dial to cooperate with indicia on the dial to indicate a flow setting of the regulator.

24. An IV flow rate regulator for an IV administration system comprising:

(a) a housing having a sidewall having stop means on said sidewall;

(b) a flow outlet extending axially from the housing having an outlet orifice;

(c) a flow inlet connected to said housing;

(d) said housing defining a metering orifice communicating with said flow inlet;

(e) a flexible flow control member extending across said metering orifice;

(f) rotatable regulating means cooperable with said flexible flow control member being advanceable and retractable to establish a selected rate of flow through said metering orifice directed to said flow outlet;

(g) a manually rotatable dial operably connected to said rotatable regulating means, said dial carrying flow rate indicia;

(h) detent means carried on said rotatable dial, said detent means cooperable with said stop means, said detent means having ridges defining a groove that defines a first position upon dial rotation in which the detent means and stop means are in registry which establishes a KVO flow position and a second dial position upon further dial rotation in which the detent and stop means prevent further dial rotation to establish a flow blocking position;

(i) a flexible membrane having an annular flange and a thinner central control section, said thinner central control section disposed across said outlet orifice to control the rate of fluid flow to substantially maintain said selected flow rate independent of pressure variations in the IV system; and (j) an indicator positioned on an outer surface of the inlet and positioned adjacent an outer edge of the dial to cooperate with indicia on the dial to indicate a flow setting of the regulator.

* * * * *